(12) United States Patent
Yamada (10) Patent No.: US 10,179,799 B2
(45) Date of Patent: Jan. 15, 2019

(54) METHOD FOR PRODUCING P1,P4-DI(URIDINE 5'-) TETRAPHOSPHATE

(71) Applicant: YAMASA CORPORATION, Choshi-shi (JP)

(72) Inventor: Kohei Yamada, Choshi (JP)

(73) Assignee: YAMASA CORPORATION, Choshi-shi (JP)

(*) Notice: Subject to any disclaimer, the term of this patent is extended or adjusted under 35 U.S.C. 154(b) by 107 days.

(21) Appl. No.: 14/758,102

(22) PCT Filed: Dec. 10, 2013

(86) PCT No.: PCT/JP2013/083100
§ 371 (c)(1),
(2) Date: Jun. 26, 2015

(87) PCT Pub. No.: WO2014/103704
PCT Pub. Date: Jul. 3, 2014

(65) Prior Publication Data
US 2016/0194347 A1    Jul. 7, 2016

(30) Foreign Application Priority Data
Dec. 28, 2012  (JP) .................. 2012-287578

(51) Int. Cl.
| C07H 19/10 | (2006.01) |
| A61K 31/7072 | (2006.01) |
| A61K 31/7105 | (2006.01) |
| C07F 9/6558 | (2006.01) |

(52) U.S. Cl.
CPC ......... *C07H 19/10* (2013.01); *A61K 31/7072* (2013.01); *A61K 31/7105* (2013.01); *C07F 9/65586* (2013.01)

(58) Field of Classification Search
None
See application file for complete search history.

(56) References Cited

U.S. PATENT DOCUMENTS

| 8,193,338 B2 * | 6/2012 | Kogo .................. C07H 19/10 536/124 |
| 2009/0299048 A1 | 12/2009 | Yanachkov et al. |
| 2010/0016567 A1 | 1/2010 | Kogo et al. |

FOREIGN PATENT DOCUMENTS

| EP | 2 045 257 A1 | 4/2009 |
| WO | 2008 012949 | 1/2008 |
| WO | 2008 024169 | 2/2008 |

OTHER PUBLICATIONS

Bastin, R. J. et al., Organic Process Research & Development, "Salt Selection and Optimisation Procedures for Pharmaceutical New Chemical Entities", 2000, vol. 4, pp. 427-435.*

Extended European Search Report dated Aug. 18, 2016 in Patent Application No. 13869663.8.
Sammy R. Shaver, et al., "Structure-activity relationships of dinucleotides: Potent and selective agonists of P2Y receptors" Purinergic, Signalling, vol. 1, No. 2, XP019775791, 2005, pp. 183-191.
Pendergast, W., et al., "Synthesis and P2Y Receptor Activity of a Series of Uridine Dinucleoside 5'-Polyphosphates", Bioorganic & Medicinal Chemistry Letters, vol. 11, (2001), (pp. 157-160).
Yanachkov, I.B., et al., "P1,P2-Diimidazolylderivatives of pyrophosphate and bis-phosphonates-synthesis, properties, and use in preparation of dinucleoside tetraphosphates and analogs", Org. Biomol. Chem., (2011), vol. 9, (pp. 730-738).
Shimazu, M., et al., "Facile Synthesis of Nucleotides Containing Polyphosphates by Mn(II) and Cd(II) Ion-Catalyzed Pyrophosphate Bond Formation in Aqueous Solution", Tetrahedron Letters, vol. 31, No. 2, (1990), (pp. 235-238).
Huang, K., et al., "Engineering Human Fhit, a Diadenosine Triphosphate Hydrolase, into an Efficient Dinucleoside Polyphosphate Synthase", J. Am. Chem. Soc., vol. 126, No. 31, (2004), (pp. 9548-9549).
International Search Report and Written Opinion of the International Searching Authority dated Jan. 21, 2014 in PCT/JP2013/083100 Filed Dec. 10, 2013.

* cited by examiner

*Primary Examiner* — Layla D Berry
*Assistant Examiner* — Bahar Craigo
(74) *Attorney, Agent, or Firm* — Oblon, McClelland, Maier & Neustadt, L.L.P.

(57) ABSTRACT

A method for producing $P^1,P^4$-di(uridine 5'-)tetraphosphate ($UP_4U$) that can avoid reduction of the synthetic efficiency without using UTP free is developed.
A method for producing $UP_4U$ comprising reacting a phosphoric acid-activating compound represented by formula [II] or [III] with a phosphoric acid compound selected from the group consisting of UMP, UDP, UTP and a pyrophosphoric acid or a salt thereof (excluding UTP free) in water or a hydrophilic organic solvent, in the presence of a metal ion selected from the group consisting of an iron (II) ion, an iron (III) ion, a trivalent aluminum ion, a trivalent lanthanum ion, and a trivalent cerium ion.
where, in the formula [II], $R^1$ represents a uridyl group binding to the 5'-position, X represents a heterocyclic group, and n represents an integer of 1 or 2,
where, in the formula [III], X represents a heterocyclic group selected from the group consisting of an imidazolyl group, a benzimidazolyl group, and a 1,2,4-triazolyl group.

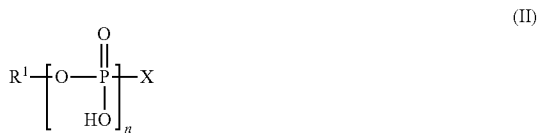

(II)

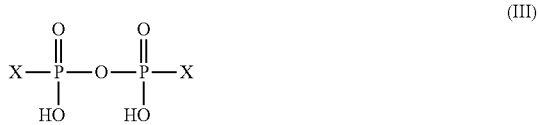

(III)

10 Claims, 6 Drawing Sheets

METHOD FOR PRODUCING P1,P4-DI(URIDINE 5'-) TETRAPHOSPHATE

CROSS-REFERENCE TO RELATED APPLICATIONS

This application is a National Stage of PCT/JP2013/083100, which was filed on Dec. 10, 2013. This application is based upon and claims the benefit of priority to Japanese Application No. 2012-287578, which was filed on Dec. 28, 2012.

TECHNICAL FIELD

The present invention relates to an effective novel method for producing $P^1,P^4$-di(uridine 5'-)tetraphosphate.

BACKGROUND ART $P^1,P^4$-di(uridine 5'-)tetraphosphate (hereinafter written as "UP$_4$U") represented by the following formula [I] or a salt thereof is used as a therapeutic drug for keratoconjunctive epithelium disorder accompanying dry eye, and is also a compound having an expectoration-inducing effect and thus is envisaged to be developed as an expectorant or a therapeutic drug for pneumonia.

Conventionally, as a method for synthesizing UP$_4$U, there have been reported a method of reacting uridine 5'-cyclic triphosphoric acid prepared by dehydration condensation of uridine 5'-triphosphoric acid (UTP) with uridine 5'-monophosphoric acid (UMP) (Non Patent Document 1) and an improved method thereof (Patent Document 1).

[I]

CITATION LIST

Patent Documents

Patent Document 1: WO 2008/012949 A
Patent Document 2: WO 2008/024169 A

Non Patent Documents

Non Patent Document 1: Bioorg. & Medicinal Chemistry Letters, vol. 11, 157 to 160 (2001),
Non Patent Document 2: Org. Biomol. Chem., 2011, No. 9, 730 to 738 (2011)

SUMMARY OF INVENTION

Technical Problem

However, the prior art described in the above documents had room for improvement in the following points.

First, the method of Patent Document 1 can synthesize UP$_4$U in a high yield of 80% or more at a laboratory level, but poses problems in mass production on the industrial scale by the method.

Specifically, in the method of Patent Document 1, it is necessary to use a starting material UTP in a salt form of a tertiary amine such as tri-n-butylamine, in order to carry out a reaction to form 5'-cyclic triphosphoric acid from 5'-UTP. Therefore, a process for previously making a trisodium salt of UTP into a free UTP (UTP free) by an ion exchange column chromatography, and then forming a salt with a tertiary amine is necessary. However, as is verified in the test examples set forth below, UTP free is very unstable material, thus it is very difficult to use UTP free as a starting material in mass production on the industrial scale.

Second, in order to efficiently synthesize 5'-cyclic triphosphoric acid from UTP, it is necessary to keep tri-n-butylamine salt of UTP in a dehydrated state immediately before the reaction. However, as is verified also in the comparison test set forth below, in mass production on the industrial scale, when tri-n-butylamine salt of UTP is azeotropically dehydrated, a thermal decomposition reaction of UTP occurs, and thus the purity of UTP is reduced, and consequently the synthetic efficiency is reduced.

As described above, it cannot be said that the method of Patent Document 1 using UTP as a starting material is an optimal process for the industrial mass production of UP$_4$U. Therefore, an object of the present invention is to develop a new production process that can avoid reduction of the synthetic efficiency due to the decomposition of a starting material, by not using UTP free, or by avoiding dehydration operation of UTP salt for synthesizing uridine 5'-cyclic triphosphoric acid.

Solution to Problem

As a method of avoiding the problems in the synthesis method described in Patent Document 1, the following two methods shown in the following A and B are considered, or have been already known.

(A) A method for synthesizing UP$_4$U, using UMP not UTP as a starting material, by preparing UTP from UMP in the reaction system, and then applying the method of Patent Document 1 without purification (hereinafter "one pot synthesis method").

(B) A method for synthesizing UP$_4$U by activating a pyrophosphoric acid by imidazole to synthesize diimidazolyl pyrophosphate and condensing it with UMP (hereinafter "old diimidazolyl pyrophosphate method", Patent Document 2, Non Patent Document 2).

However, the one pot synthesis method and the old diimidazolyl pyrophosphate method both performed using an organic solvent such as dimethylformamide (DMF) as a solvent of synthesis reaction of UP$_4$U under anhydrous environment. On the other hand, UMP, UTP, pyrophosphoric acid and the like used as the starting materials of the reaction are all highly hydrophilic compound, thus these starting materials must undergo a dehydration step in each process, in order to be subjected to the reaction. Particularly, a pyrophosphate had a problem that solubility in an organic solvent is also poor, handling requires caution, and the like.

Also, the present inventors further studied for the above two improved synthesis methods. First, when the one pot synthesis method was studied in detail, the yield of the target product UP$_4$U was largely lowered to about 40%, as shown in the examples set forth below. In addition, when the method of Patent Document 1 was carried out as the one pot synthesis method, various by-products were generated, thus it was revealed that complex purification by a column chromatography is necessary for the separation.

Next, the old diimidazolyl pyrophosphate method was also studied in detail. As a result, it was newly found that by-products were much generated also in the old diimidazolyl pyrophosphate method, and the yield of UP$_4$U, a final product, relative to UMP is far from high, as shown in the examples set forth below. More specifically, it became clear that both the one pot method and the old diimidazolyl pyrophosphate method cannot be said as a synthesis method suitable for UP$_4$U mass production on the industrial scale.

Therefore, the present inventors have conducted extensive studies to establish an efficient method for synthesizing UP$_4$U suitable for industrial mass production, and consequently have found that, by a simple method of combining (a) a phosphoric acid-activating compound synthesized by condensing uridine 5'-diphosphoric acid (UDP), UMP or a pyrophosphoric acid with a compound selected from the group consisting of imidazole, benzimidazole and 1,2,4-triazole optionally having a substituent, and (b) a phosphoric acid compound selected from the group consisting of UMP, UDP, UTP and a pyrophosphoric acid or a salt thereof (excluding UTP free), and reacting the compounds in water or a hydrophilic organic solvent, in the presence of a metal ion selected from the group consisting of an iron (II) ion, an iron (III) ion, a trivalent aluminum ion, a trivalent lanthanum ion and a trivalent cerium ion, as a catalyst, use of UTP free and dehydration operation of UTP salt could be avoided, and UP$_4$U could be synthesized in a high yield with less by-product. The present invention has been accomplished on the basis of this finding.

More specifically, the present invention provides a method for producing P$^1$,P$^4$-di(uridine 5'-)tetraphosphate, comprising reacting a phosphoric acid-activating compound represented by the following formula [II] or [III] with a phosphoric acid compound selected from the group consisting of UMP, UDP, UTP and a pyrophosphoric acid or a salt thereof (excluding UTP free) in water or a hydrophilic organic solvent, in the presence of a metal ion selected from the group consisting of an iron (II) ion, an iron (III) ion, a trivalent aluminum ion, a trivalent lanthanum ion and a trivalent cerium ion.

[II]

wherein R$^1$ represents an uridyl group binding to the 5'-position; X represents a heterocyclic group selected from the group consisting of an imidazolyl group, a benzimidazolyl group and a 1,2,4-triazolyl group; and n represents an integer of 1 or 2.

[III]

wherein X represents a heterocyclic group selected from the group consisting of an imidazolyl group, a benzimidazolyi group and a 1,2,4-triazolyl group.

Advantageous Effects of Invention

The production method of the present invention can synthesize UP$_4$U in a high yield while avoiding use of UTP free and dehydration operation of UTP salt. Also, in the production method of the present invention, almost no by-product is produced, thus purification of the synthesized UP$_4$U is easy. Furthermore, a reaction is carried out under hydrophilic conditions, whereby a complicated dehydration step can be omitted. More specifically, the production method of the present invention is extremely suitable for industrial mass synthesis of UP$_4$U.

DESCRIPTION OF EMBODIMENTS

Hereinbelow, the embodiment of the present invention will be described in detail.

<Phosphoric Acid-Activating Compound>

The phosphoric acid-activating compound used in the present invention is a compound represent by the formula [II] or [III], and synthesized by condensing UMP, UDP or a pyrophosphoric acid with imidazole, benzimidazole or 1,2,4-triazole optionally having a substituent.

[II]

wherein R$^1$ represents an uridyl group binding to the 5'-position; X represents a heterocyclic group selected from the group consisting of an imidazolyl group, a benzimidazolyl group and a 1,2,4-triazolyl group; and n represents an integer of 1 or 2.

[III]

wherein X represents a heterocyclic substituent selected from the group consisting of an imidazolyl group, a benzimidazolyl group and a 1,2,4-triazolyl group.

The heterocyclic substituent represented by X includes an imidazolyl group, a benzimidazolyl group, a 1,2,4-triazolyl group, and the like. Also, these heterocyclic groups may have a substituent in the heterocyclic group, and examples of the substituent include $C_1$-6 alkyl groups, nitro groups, cyano groups, and the like.

The phosphoric acid-activating compound described above specifically includes UDP-imidazolide, UDP-triazolide, UMP-imidazolide, dimidazolyl pyrophosphate, and the like, and these compounds can be prepared according to a known method (Nucleic Acids Research, vol. 4, 2843 (1977), Journal of American Chemical Society, vol. 126, 9548 (2004)).

In the synthesis of $UP_4U$, a mixture of the phosphoric acid-activating compound such as UDP-imidazolide, UDP-triazolide, UMP-imidazolide or dimidazolyl pyrophosphate or a concentrated solution thereof can be used as it is or used after purified as necessary.

<Phosphoric Acid Compound>

The phosphoric acid compound of the present invention is a compound represented by the following formula (IV) or a salt thereof, and specifically includes UMP, UDP, UTP, a pyrophosphoric acid and salts thereof, except for UTP free.

[IV]

wherein $R^2$ represents an uridyl group binding to the hydrogen atom or the 5'-position; and m represents an integer of 1 to 3.

The phosphoric acid compound can be used in the form of an alkali metal salt such as sodium and potassium, a tertiary ammonium salt such as triethylammonium and tributylammonium, and a quaternary ammonium salt such as tetraethylammonium salt and tetrabutylammonium.

<Combination of Starting Material Compounds>

The combination of the starting material compounds of the phosphoric acid-activating compound and the phosphoric acid compound described above may be appropriately determined, and it is suitable to use preferably in the following combinations.

Combination 1: Combination of UDP-activating compound and UDP or UDP salt

Combination 2: Combination of UMP-activating compound and UTP salt

Combination 3: Combination of UMP-activating compound and pyrophosphoric acid or pyrophosphate Combination 4: Combination of pyrophosphoric acid-activating compound and UMP or UMP salt In any combination, it is preferred when the molar ratio of the phosphoric acid-activating compound and the phosphoric acid compound in the condensation reaction is set to the range of 1:10 to 10:1, since the yield of $UP_4U$ is improved. The molar ratio is, for example, (1) In Combination 1 above, the molar ratio is either 3:8, 4:7, 5:6, 6:5, 7:4, 8:3, 9:2, or 10:1, (2) In Combination 2 above, the molar ratio is either 1:10, 2:9, 3:8, 4:7, 5:6, 6:5, 7:4, or 8:3, (3) In Combination 3 above, the molar ratio is either 4:7, 5:6, 6:5, 7:4, 8:3, 9:2, or 10:1, and further, (4) In Combination 4 above, the molar ratio is either 4:7, 5:6, 6:5, 7:4, 8:3, 9:2, or 10:1, and also may be within the range of either two numerical values exemplified here.

<Metal Ion>

The metal ion used in the present invention is added to a solution, in the form of a metal salt containing a target metal ion, thereby becoming a metal ion in water or a hydrophilic organic solvent, and can be provided to the reaction system. As the kind of the metal salt, a metal halide, a metal inorganic salt, a metal organic salt, and the like can be suggested. As further specific examples, it is preferred to use (i) ferrous chloride, ferric chloride, ferric bromide, aluminum trichloride, cerium trichloride, lanthanum trichloride and the like as examples of the metal halide, (ii) inorganic salts such as sulfate, nitrate, perchloric acid and the like of a metal selected from the group consisting of iron (divalent), iron (trivalent), aluminum, cerium and lanthanum as examples of the metal inorganic salt, and (iii) trifluoromethanesulfonate, acetate, trifluoroacetate, citrate and the like of a metal selected from the group consisting of iron (divalent), iron (trivalent), aluminum, cerium and lanthanum as examples of the metal organic salt, since the yield of $UP_4U$ is improved. Among them, a ferric salt is preferable, and ferric chloride is particularly preferable, from the viewpoint of synthesis yield and ease in handling. Here, the metal salt to be used may be anhydride or hydride. However, among the combinations of the phosphoric acid-activating compound and the phosphoric acid compound, particularly in the case of Combination 4, it is particularly preferable to use iron (III) ion, trivalent aluminum ion or the like.

In order to improve the yield of $UP_4U$, the metal salt that is a metal ion source, is preferably used in a molar amount of 0.001 to 10 times the total molar number of the phosphoric acid compound used in the reaction, and particularly preferably used in a molar amount of 0.001 to 1 times. For example, the amount of this metal salt is any of molar amounts of 0.001, 0.005, 0.01, 0.05, 0.1, 0.5 and 1 times the total molar number of the phosphoric acid compound used in the reaction, and may be within any two numerical values exemplified here.

<Conditions of Condensation Reaction and Purification>

The condensation reaction of the phosphoric acid-activating compound and the phosphoric acid compound in the present invention is performed using water or a hydrophilic organic solvent as a solvent. From the viewpoint of synthesis yield and ease in handling, alcohols having six or less carbon atoms such as methanol and ethanol, ketones such as acetone, ethers such as dioxane, nitriles such as acetonitrile, and amides such as dimethylformamide can be used as the hydrophilic organic solvent.

In this condensation reaction, the reaction pH is preferably 7 or less, and particularly preferably around 1 to 4, in order to improve the yield of $UP_4U$. Also, in this condensation reaction, the reaction temperature is preferably 0° C. to 60° C., in order to improve the yield of $UP_4U$. In the combination of the above starting material compounds, a reaction temperature of 20 to 30° C. is particularly preferable in the case of Combination 1 to Combination 3, and a reaction temperature of 0 to 20° C. is particularly preferable in the case of Combination 4. The time period of this condensation reaction is preferably 1 to 36 hours or so, and particularly preferably 2 to 20 hours, in order to perform necessary and sufficient condensation reaction.

After the completion of the condensation reaction, methods used for general isolation purification of nucleotide (e.g., crystallization method, ion exchange column chromatography, adsorption column chromatography, activated carbon column chromatography, etc.) are appropriately combined, whereby the produced $UP_4U$ can be separated and purified, and also can be provided in the form of salt as necessary.

As the ion-exchange resin used in ion-exchange column chromatography, a strongly basic anion-exchange resin (e.g., Amberlite IRA 402 [manufactured by Rohm & Haas], Diaion PA-312 or Diaion SA-11A [manufactured by Mitsubishi Chemical Corporation]), a weakly basic anion-exchange resin (e.g., Amberlite IRA 67 [manufactured by Rohm & Haas] or Diaion WA-30 [manufactured by Mitsubishi Chemical Corporation]), a strongly acidic cation-exchange resin (e.g., Diaion PK-216 [manufactured by Mitsubishi Chemical Corporation]), a weakly basic cation-exchange resin (e.g., Diaion WK-30 [manufactured by Mitsubishi Chemical Corporation]) or the like can be used.

The activated carbon used may be ground or granulated activated carbon for chromatography, for example, activated carbon commercially available from Wako Pure Chemical Industries, Ltd., Futamura Chemical Co., Ltd or the like can be used.

Also, a known method may be used for crystallization, and the crystal is obtained by adding a hydrophilic organic solvent to the obtained $UP_4U$ or a salt thereof for precipitation of crystals. Examples of the hydrophilic organic solvent used include alcohols having six or less carbon atoms such as methanol and ethanol, ketones such as acetone, ethers such as dioxane, nitriles such as acetonitrile, amides such as dimethylformamide, and the like. Alcohols are preferable, and further, ethanol is particularly preferable.

<Action Effect of Present Invention>

As described above, in the present invention, a method of combining (a) a phosphoric acid-activating compound synthesized by condensing uridine 5'-diphosphoric acid (UDP), UMP or a pyrophosphoric acid with a compound selected from the group consisting of imidazole, benzimidazole and 1,2,4-triazole optionally having a substituent, and (b) a phosphoric acid compound selected from the group consisting of UMP, UDP, UTP and a pyrophosphoric acid or a salt thereof (excluding UTP free), and reacting the compounds in water or a hydrophilic organic solvent, in the presence of a metal ion selected from the group consisting of an iron (II) ion, an iron (III) ion, a trivalent aluminum ion, a trivalent lanthanum ion and a trivalent cerium ion, as a catalyst, is used, whereby the industrial mass production of $UP_4U$ can be carried out by a simple method as shown in the examples set forth below.

On the other hand, as already explained, the conventionally known method of Patent Document 1 can synthesize $UP_4U$ in a high yield of 80% or more at a laboratory level, but poses problems in mass production on the industrial scale by the method. Specifically, in the method of Patent Document 1, it is necessary to use a starting material UTP in a salt form of a tertiary amine such as tri-n-butylamine, in order to carry out a reaction to form 5'-cyclic triphosphate of uridine. Therefore, a process for previously making a trisodium salt of UTP into free UTP (UTP free) by ion exchange column chromatography, and then forming a salt with a tertiary amine is necessary. However, as is verified in the test examples set forth below, UTP free is very unstable material, thus it is very difficult to use UTP free as a starting material in mass production on the industrial scale. Also, in order to efficiently synthesize a reaction to form 5'-cyclic triphospate of uridine, it is necessary to keep tri-n-butylamine salt of UTP in a dehydrated state immediately before the reaction. However, as is shown in the comparison test set forth below, in mass production on the industrial scale, when tri-n-butylamine salt of UTP is azeotropically dehydrated, a thermal decomposition reaction of UTP occurs, and thus the purity of UTP is reduced, and consequently the synthetic efficiency is reduced.

Also, in the method of Patent Document 2 and Non Patent Document 2, it was possible to synthesize $UP_4U$ without using the step using UTP free, but the yield relative to UMP was markedly lowered, as also shown in the comparative examples set forth below. In addition, by-products were much generated, and it could not be said as production method suitable for industrial large-scale production.

On the other hand, in the method of the present invention, since the starting material is UDP or UMP, it is not necessary to use UTP free, and further, dehydration operation of UTP salt for synthesizing uridine 5'-cyclic triphosphate can also be avoided, thus reduction of the synthetic efficiency due to decomposition of the starting materials can be avoid, as shown in the examples set forth below. Also, it is not necessary to azeotropically dehydrate a tri-n-butylamine salt of UTP, a thermal decomposition reaction of UTP does not occur, and also the purity of UTP is not reduced by generating unnecessary by-product, as shown in the examples set forth below. Therefore, the production method of the present invention is an extremely suitable method for industrial mass synthesis of $UP_4U$.

In the present invention, it is preferable that the phosphoric acid-activating compound is UDP-imidazolide, and the phosphoric acid compound is UDP or a UDP salt. It is because, in this case, it is verified in the examples set forth below that synthesis of $UP_4U$ can be performed in a high yield while avoiding use of UTP free and dehydration operation of UTP salt that are not suitable for industrial mass production.

In addition, in the present invention, it is preferable that the phosphoric acid-activating compound is UMP-imidazolide, and the phosphoric acid compound is UTP or a UTP salt. It is because, also in this case, it is verified in the examples set forth below that synthesis of $UP_4U$ can be performed in a high yield while avoiding use of UTP free and dehydration operation of UTP salt that are not suitable for industrial mass production.

In addition, in the present invention, it is preferable that the phosphoric acid-activating compound is UMP-imidazolide, and the phosphoric acid compound is a pyrophosphoric acid or a pyrophosphoric acid salt. It is because, also in this case, it is verified in the examples set forth below that synthesis of $UP_4U$ can be performed in a high yield while avoiding use of UTP free and dehydration operation of UTP salt that are not suitable for industrial mass production.

In addition, in the present invention, it is preferable that the phosphoric acid-activating compound is diimidazolyl pyrophosphate, and the phosphoric acid compound is UMP or a UMP salt. It is because, also in this case, it is verified in the examples set forth below that synthesis of $UP_4U$ can be efficiently performed while avoiding use of UTP free and dehydration operation of UTP salt that are not suitable for industrial mass production.

In addition, in the present invention, it is preferable that the metal ion is selected from the group consisting of an iron (II) ion, an iron (III) ion and an aluminum ion. Particularly when the phosphoric acid-activating compound is diimidazolyl pyrophosphate, and the phosphoric acid compound is UMP free or a UMP salt, it is preferable that the metal ion is selected from the group consisting of an iron (III) ion and an aluminum ion. It is because, also in this case, it is verified in the comparative examples set forth below that synthesis of $UP_4U$ can be efficiently performed, as compared with the case of using other metal ion.

In addition, in the present invention, it is preferable that the metal ion is supplied in a salt form selected from the group consisting of chloride, bromide, nitrate, sulfate and acetate of the metal. It is because, also in this case, it is verified that synthesis of $UP_4U$ can be efficiently performed.

While the embodiments of the present invention are described as above, these are illustrations of the present invention, and various constitutions other than the above also can be also adopted.

EXAMPLES

Hereinbelow, the present invention will be further described in detail by way of examples, which should not be construed as limiting the present invention thereto.

Example 1

Combination 1 (Part 1): Reaction of UDP-imidazolide (where, in the formula II, $R^1$=5'-uridyl, X=imidazolyl, n=2) and UDP sodium salt (where, in the formula IV, $R^2$=5'-uridyl, m=2)

Dimethylacetamide (6.0 ml) was added to an aqueous solution of 0.32 M UDP-tributylamine salt (1.26 ml, 4.0 mmol), and the mixture was azeotropically dehydrated four times. The resulting residue was dissolved in dimethylacetamide (6.0 ml), and carbonyldiimidazole (1.95 g, 12.0 mmol) was added thereto, then the mixture was stirred at room temperature for 1 hour. Water (0.2 ml) was added to the reaction mixture under ice cooling, and further, a 0.5 M aqueous hydrochloric acid solution (12.0 ml) was added dropwise (pH 7.0). The reaction mixture was concentrated under reduced pressure to prepare a UDP-imidazolide solution.

An aqueous UDP sodium solution (2.0 mmol, 2.1 ml) was added to the UDP-imidazolide solution under ice cooling, and further, a 2 M aqueous hydrochloric acid solution was added thereto to make a mixed solution with pH 4.9. A 1 M aqueous ferric chloride solution (1.5 mmol, 1.5 ml) was added thereto under ice cooling, and further, a 2 M aqueous hydrochloric acid solution was added thereto to make a mixed solution with pH 1.6, and the mixed solution was stirred at 25° C. for 3 hours. The reaction mixture was adjusted to pH 12 by adding an aqueous 6 M sodium hydroxide solution, and stirred at room temperature for 30 minutes. The reaction mixture was adjusted to pH 7.6 by adding 2 M hydrochloric acid. The resulting reaction mixture was quantitatively determined by HPLC analysis, and the synthesis yield of $UP_4U$ was calculated as 87%.

The mixture was concentrated to 10 ml, and dissolved by adding sodium hydrogen phosphate (4.2 mmol) to deposit iron phosphate. The suspension was left to stand at 4° C. overnight, then the precipitate was removed by centrifugation. The supernatant was adjusted to pH 2.5, and then adjusted to a 30 ml solution to prepare a column adsorbing solution.

Desalting of the column adsorbing solution was performed by activated carbon column chromatography (resin amount of 20 ml), and the resulting recovery solution was adjusted to pH 7 and concentrated, then subjected to membrane filtration. The residue was further concentrated, and ethanol was added dropwise to the residue, then crystallized at room temperature overnight. The crystal was filtered and vacuum-dried at 50° C. for 3 hours to obtain 2.12 g (yield of 75% as tetrahydrate) of $UP_4U$.

Example 2

Combination 1 (Part 2): Reaction of UDP-imidazolide (where, in the formula II, $R^1$=5'-uridyl, X=imidazolyl, n=2) and UDP sodium salt (where, in the formula IV, $R^2$=5'-uridyl, m=2)

A 5.64 M imidazole-dimethylacetamide solution (0.5 ml) was added to a 0.94 M aqueous UDP sodium solution (1.0 ml), and N,N-diisopropylcarbodiimide (0.73 ml, 4.7 mmol) was added at room temperature, and stirred at room temperature for 5 hours at 50° C. for 2 hours to prepare a mixture of UDP and a UDP-imidazolide.

A 2 M aqueous hydrochloric acid solution was added thereto under ice cooling to make a mixed solution with pH 5.3. Thereafter, a 1 M aqueous ferric chloride solution (0.24 mmol, 0.24 ml) was added thereto, and a 2 M aqueous hydrochloric acid solution was further added thereto to make a mixed solution with pH 1.9, and the mixed solution was stirred at 25° C. for 16 hours. The resulting reaction mixture was quantitatively determined by HPLC analysis, and the yield of $UP_4U$ was calculated as 63%.

Example 3

Combination 1 (Part 3): Reaction of UDP-imidazolide (where, in the formula II, $R^1$=5'-uridyl, X=imidazolyl, n=2) and UDP sodium salt (where, in the formula IV, $R^2$=5'-uridyl, m=2)

Propionitrile (3.0 ml) was added to an aqueous solution of 0.17 M UDP-tributylamine salt (11.8 ml, 2.0 mmol), and the mixture was azeotropically dehydrated four times. The resulting residue was dissolved in propionitrile (3.0 ml). This solution was added dropwise to a propionitrile (2.0 ml) suspension of 1,1'-carbonyldiimidazole (0.97 g, 6.0 mmol). The reaction mixture was stirred at room temperature for 30 minutes and then concentrated under reduced pressure to prepare a UDP-imidazolide solution.

UDP-disodium salt (0.53 g, 1.0 mmol) was added to the UDP-imidazolide solution under ice cooling, and the mixed solution was adjusted to pH 3.9 by a 6 M aqueous hydrochloric acid solution. A 1 M aqueous ferric chloride solution (15 µl, 0.02 mmol) was further added thereto, and the mixed solution was stirred at 10° C. for 27 hours. The reaction mixture was adjusted to pH 10 by adding a 7.5 M aqueous sodium hydroxide solution, and then stirred for 1 hour under ice cooling. 10 ml of ethanol was added to the reaction mixture under ice cooling, and the mixture was left to stand at 4° C. overnight. The precipitate was collected and prepared to a 20 ml aqueous solution with pH 7.5, then the aqueous solution quantitatively determined by HPLC analysis, and the yield of $UP_4U$ was calculated as 94%. More specifically, it has been revealed that even when the amount of ferric chloride catalyst used is greatly reduced, the reaction progresses well.

Example 4

Combination 1 (Part 4): Reaction of UDP-benzimidazolide (where, in the formula II, $R^1$=5'-uridyl, X=benzimidazolyl, n=2) and UDP sodium salt (where, in the formula IV, $R^2$=5'-uridyl, m=2)

UDP-disodium salt (0.5 g, 0.94 mmol) was dissolved in 2.7 ml of water, and a dimethylacetamide solution (1.8 ml) of benzimidazole (0.33 g, 2.82 mmol) and N,N-diisopropylcarbodiimide (0.44 ml, 2.82 mmol) were added, and the mixture was stirred at room temperature overnight. The solvent was distilled under reduced pressure to prepare a mixture of UDP and UDP-benzimidazolide.

1 ml of water was added thereto, and then a 2 M aqueous hydrochloric acid solution was added thereto under ice cooling to adjust pH to 4.6. A 1 M aqueous ferric chloride solution (94 μl, 0.09 mmol) was added thereto under ice cooling, and a 2 M aqueous hydrochloric acid solution was further added thereto to make a mixed solution with pH 3.0, and the mixed solution was stirred at room temperature for 10 hours. The reaction mixture was adjusted to pH 12 by adding an aqueous 6 M sodium hydroxide solution, and stirred at room temperature for 1 hour. The reaction mixture was adjusted to pH 7.3 by adding 2 M hydrochloric acid. The resulting mixture was quantitatively determined by HPLC analysis, and the yield of $UP_4U$ was calculated as 83%.

Example 5

Combination 1 (Part 5): Reaction of UDP-triazolide (where, in the formula II, $R^1$=5'-uridyl, X=1,2,4-triazolyl, n=2) and UDP sodium salt (where, in the formula IV, $R^2$=5'-uridyl, m=2)

Dimethylacetamide (2.0 ml) was added to an aqueous solution of 0.37 M UDP-tributylamine salt (1.6 ml, 0.6 mmol), and the mixture was azeotropically dehydrated four times. The resulting residue was dissolved in dimethylacetamide (2.0 ml), and 1,1'-carbonyldi-(1,2,4-triazole) (0.25 g, 1.5 mmol) was added thereto, then the mixed solution was stirred at room temperature for 1 hour. Water (0.2 ml) was added to the reaction solution under ice cooling, and further, a 0.5 M aqueous hydrochloric acid solution was added to have pH 7.4. The mixture was concentrated under reduced pressure to prepare a UDP-triazolide solution.

An aqueous UDP sodium solution (0.25 mmol, 0.9 ml) was added to the UDP-triazolide solution under ice cooling, and a 1 M aqueous ferric chloride solution (0.19 mmol, 0.19 ml) was added (pH 6.3), and the mixture was stirred at 25° C. for 5 hours. The mixture was adjusted to pH 12 by adding an aqueous 6 M sodium hydroxide solution, and stirred at room temperature for 30 minutes. The mixture was adjusted to pH 7.0 by adding 2 M hydrochloric acid. The resulting mixture was quantitatively determined by HPLC analysis, and the yield of $UP_4U$ was calculated as 48%.

Example 6

Combination 2: Reaction of UMP-imidazolide (where, in the formula II, $R^1$=5'-uridyl, X=imidazolyl, n=1) and UTP sodium salt (where, in the formula IV, $R^2$=5'-uridyl, m=3)

Tributylamine (0.25 ml, 1.1 mmol) was added to a 2.05 M aqueous UMP free solution (0.49 ml, 1.0 mmol), and the mixed solution was stirred at room temperature for 20 minutes. Then, dimethylacetamide (1.5 ml) was further added, and the mixed solution was azeotropically dehydrated three times. The resulting UMP-tributylamine salt solution was dissolved in dimethylacetamide (1.5 ml), and carbonyldiimidazole (486 mg, 3.0 mmol) was added thereto, then the mixture was stirred at room temperature for 1 hour. Water (0.2 ml) was added to the mixture under ice cooling, and further, a 0.5 M aqueous hydrochloric acid solution (4.0 ml) was added dropwise (pH 7.2). The mixture was concentrated under reduced pressure to prepare a UMP-imidazolide solution.

The UMP-imidazolide solution and a 2 M aqueous hydrochloric acid solution were added to a 165 mM aqueous UTP sodium salt solution (8.0 ml, 1.3 mmol) under ice cooling to make a mixed solution with pH 5.1. An aqueous ferric chloride solution (0.5 mmol, 0.2 ml) was added thereto under ice cooling, and the mixed solution was stirred at 25° C. for 4 hours. The mixture was subjected to membrane filtration, then adjusted to pH 10.4 by adding a 1 M aqueous sodium hydroxide solution (11 ml), and stirred at room temperature for 40 minutes. Thereafter, the mixture was adjusted to pH 6.9 by adding 2 M hydrochloric acid (3.5 ml). The resulting mixture was quantitatively determined by HPLC analysis, and the yield of $UP_4U$ was calculated as 67%.

Thereafter, as a result of purification in the same manner as in Example 1, 471 mg (50% as tetrahydrate) of an object $UP_4U$ was obtained.

Example 7

Combination 3: Reaction of UMP-imidazolide (where, in the formula II, $R^1$=5'-uridyl, X=imidazolyl, n=1) and pyrophosphoric acid triethylamine salt (where, in the formula IV, $R^2$=hydrogen atom, m=2)

Tributylamine (0.25 ml, 1.1 mmol) was added to a 2.05 M aqueous UMP free solution (0.49 ml, 1.0 mmol), and the mixed solution was stirred at room temperature for 20 minutes. Then, dimethylacetamide (1.5 ml) was further added, and the mixed solution was azeotropically dehydrated three times. The resulting UMP-tributylamine salt was dissolved in dimethylacetamide (1.5 ml), carbonyldiimidazole (486 mg, 3.0 mmol) was added thereto, and the mixed solution was stirred at room temperature for 1 hour. Water (0.2 ml) was added to the mixture under ice cooling, and further, a 0.5 M aqueous hydrochloric acid solution (4.0 ml) was added dropwise (pH 7.2). The mixture was concentrated under reduced pressure to prepare a UMP-imidazolide solution (this operation was performed twice).

An aqueous 0.95 M pyrophosphoric acid triethylamine salt solution (1.1 ml, 1.0 mmol) was added to the UMP-imidazolide solution under ice cooling, and further, a 1 M aqueous ferric chloride solution (0.5 mmol, 0.5 ml) was added thereto. The mixture was adjusted to pH 5.1 by a 2 M aqueous hydrochloric acid solution, and then stirred at 25° C. for 5 hours. After stirring, the separately prepared UMP-imidazolide solution (1.0 mmol) was added thereto under ice cooling, and the mixed solution was further adjusted to pH 2.1 by a 2 M aqueous hydrochloric acid solution, and stirred at 25° C. for 6 hours. An aqueous 6 M sodium hydroxide solution was added thereto to have pH 11, and the mixed solution was stirred at room temperature for 30 minutes. Further, the mixed solution was adjusted to pH 7.6 by adding 2 M hydrochloric acid and quantitatively determined by HPLC analysis, and the yield of $UP_4U$ was calculated as 45%.

Example 8

Combination 4: Reaction of diimidazolyl pyrophosphate (where, in the formula III, X=imidazolyl) and UMP (where, in the formula IV, $R^2$=5'-uridyl, m=1)

Tributylamine (0.95 ml, 4.0 mmol) and formamide (2.0 ml) were added to an aqueous solution of 1.09 M pyrophosphoric acid-triethylamine salt (1.86 ml, 2.0 mmol), and the mixed solution was azeotropically dehydrated with dimethylformamide four times. The resulting residue was dissolved in dimethylformamide (8.0 ml), carbonyldiimidazole (0.97 g, 6.0 mmol) was added thereto, and the mixture was stirred at room temperature for 1 hour. Water (0.2 ml) was added to the mixture under ice cooling, and further, a 2.0 M aqueous hydrochloric acid solution (1.5 ml) was added dropwise (pH 7). The mixture was concentrated under reduced pressure to prepare a diimidazolyl pyrophosphate solution.

An aqueous UMP free solution (2.03 M, 2.47 ml, 5.0 mmol) was added to the diimidazolyl pyrophosphate solution under ice cooling. Further, a 1 M aqueous ferric chloride solution (2 ml, 2.0 mmol) was added thereto, and the mixture was adjusted to pH 2.4 by adding a 2 M aqueous hydrochloric acid solution, and stirred at 0° C. for 5 hours. An aqueous 6.0 M sodium hydroxide solution was added to the mixture to have pH 6.3. Water was added thereto to prepare a 50 ml aqueous solution, and the resulting reaction solution was quantitatively determined by HPLC analysis, and the yield of $UP_4U$ was calculated as 51%.

Test Example 1

Determination of Stability of UTP and Related Compound

In order to evaluate stability of UTP free, stability of aqueous solutions of UTP free and UTP sodium salt (UTP-Na) and a dimethylacetamide solution of UTP-tributylamine salt (UTP-TBA) was examined. Also, stability of aqueous solutions of UDP free and UDP-Na as comparison control was also determined. The solution of each substance was left to stand for a certain period at −20° C., 25° C. or 50° C., and the concentration of each substance was determined by HPLC to calculate a decomposition rate. Here, the decomposition rate was defined as the following [equation 1].

Decomposition rate (%) of each substance={100−(HPLC % of each substance at determination/HPLC % of each substance at test start)×100}  [equation 1]

As a result, it was revealed that, as shown in the following [Table 1] and [Table 2], UTP free and UTP-TBA has clearly low stability during storage of the solution, as compared to other compounds such as UTP sodium salt, UDP free, and UDP sodium salt.

TABLE 1

|  | −20° C., 18 h | 25° C., 8 h | 25° C., 24 h |
| --- | --- | --- | --- |
| 16 mM UTP free | 4% | 4% | 12% |
| 10 mM UDP free | — | 0% | 0% |

(Numerical values in the table indicate a decomposition rate in each condition)

TABLE 2

|  | 50° C., 8 h | 50° C., 24 h |
| --- | --- | --- |
| 35 mM UTP-TBA | 7% | 18% |
| 40 mM UTP-Na | 2% | 6% |
| 40 mM UDP-Na | 2% | 5% |

(Numerical values in the table indicate a decomposition rate in each condition)

Comparative Test 1

Metal catalyst effect in reaction of UDP-imidazolide (where, in the formula II, $R^1$=5'-uridyl, X=imidazolyl, n=2) and UDP sodium salt (where, in the formula IV, $R^2$=5'-uridyl, m=2)

Various metal catalysts (0.06 M) were added to a mixed aqueous solution of UDP-imidazolide and UDP sodium salt at a molar ratio of 1:1 (each 0.15 M), and the mixture was adjusted to pH 2±0.3 by a 2 M aqueous hydrochloric acid solution. The produced amount of $UP_4U$ after 6 hours was quantitatively determined at 25° C. by HPLC. The result is shown in Table 3.

TABLE 3

| Catalyst | Reaction pH | Yield of $UP_4U$ |
| --- | --- | --- |
| $BFeCl_3$ | 2.0 | 79.4% |
| $Fe(NO_3)_3$ | 2.0 | 81.8% |
| $AlCl_3$ | 2.0 | 69.2% |
| $LaCl_3$ | 2.0 | 52.1% |
| $CeCl_3$ | 2.0 | 53.5% |
| $MnCl_2$ | 2.0 | 10.3% |
| $MgCl_2$ | 2.2 | 6.3% |
| $FeCl_2$ | 2.3 | 68.3% |
| $ZnCl_2$ | 2.2 | 7.0% |
| No addition | 2.1 | 2.8% |

As a result, it was revealed that $UP_4U$ can be obtained in particularly high yield when ferrous chloride, ferric chloride, ferric nitrate, aluminum chloride, lanthanum chloride or cerium chloride is used as the metal salt as the catalyst.

Comparative Test 2

Metal catalyst effect in reaction of imidazolyl pyrophosphate (where, in the formula III, X=imidazolyl) and UMP free (where, in the formula IV, $R^2$=5'-uridyl, m=1)

Various metal catalysts (0.4 mmol) were added to a mixed aqueous solution of diimidazolyl pyrophosphate and UMP free at a molar ratio of 2:5 (0.4 mmol as diimidazolyl pyrophosphate) prepared in the method of Example 8, and the mixture was adjusted to pH 2.5±0.5 by a 2 M aqueous hydrochloric acid solution. The produced amount of $UP_4U$ after 5 hours was quantitatively determined at 0° C. by HPLC. The result is shown in [Table 4].

TABLE 4

| Catalyst | Reaction pH | Yield of $UP_4U$ |
| --- | --- | --- |
| $FeCl_3$ | 2.9 | 51.1% |
| $AlCl_3$ | 2.7 | 49.2% |
| $MnCl_2$ | 2.7 | 17.7% |
| $MgCl_2$ | 2.8 | 5.2% |
| $FeCl_2$ | 2.9 | 10.6% |
| $ZnCl_2$ | 2.9 | 0.6% |
| $NiCl_2$ | 2.7 | 0.2% |
| $CoCl_2$ | 2.7 | 1.2% |

TABLE 4-continued

| Catalyst | Reaction pH | Yield of UP$_4$U |
|---|---|---|
| CaCl$_2$ | 2.8 | 0.5% |
| No addition | 2.3 | 0% |

As a result, it was revealed that UP$_4$U can be obtained in particularly high yield when ferric chloride or aluminum chloride is used as the metal salt as the catalyst when the combination of a pyrophosphoric acid-activating compound and UMP is used.

Comparative Test 3

Figure 1:
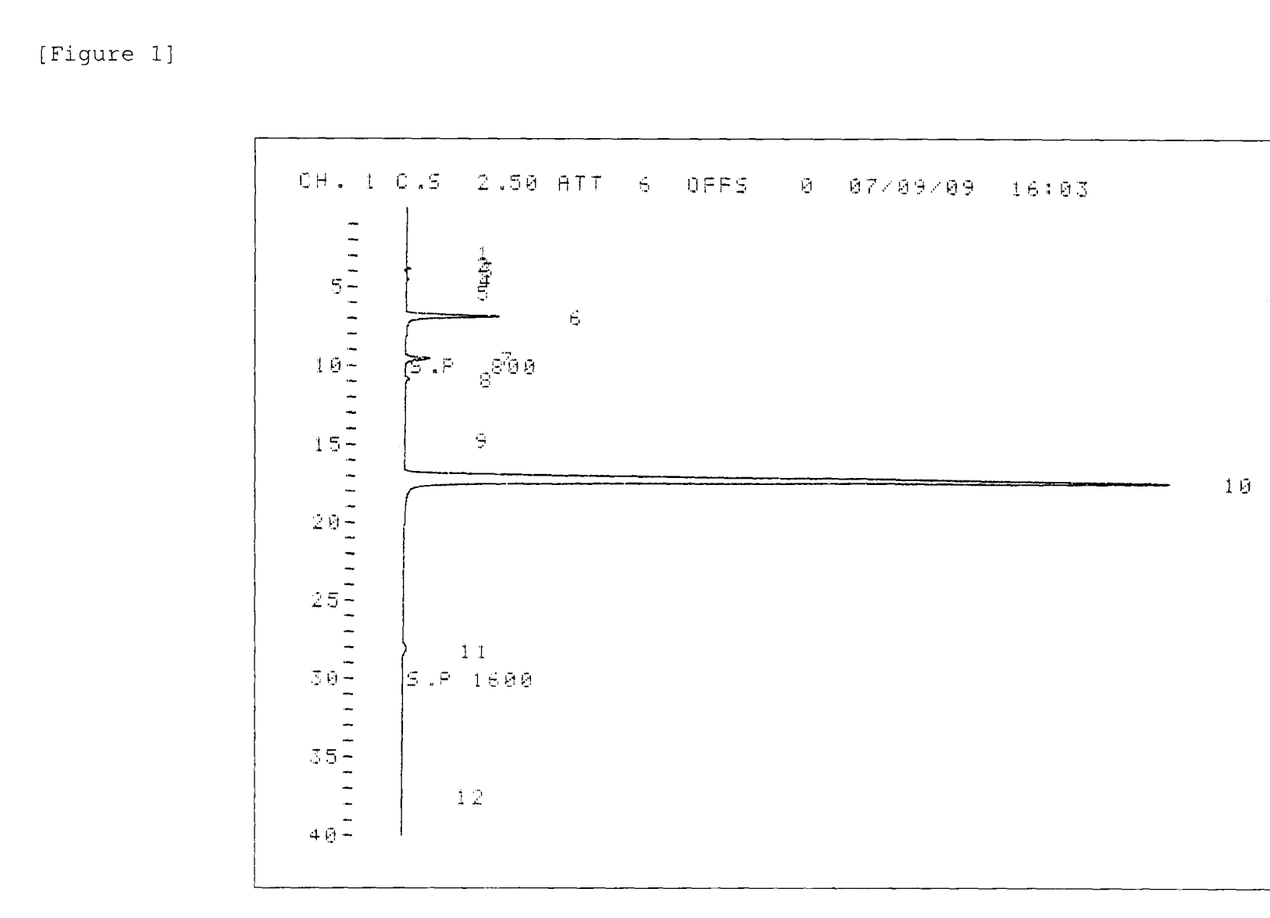
FIG. 1 illustrates an HPLC chart analyzing a product in a reaction mixture when UP$_4$U is synthesized by the method of the present invention. In the figure, the 10$^{th}$ peak illustrates a target product UP$_4$U, and the 6$^{th}$ peak illustrates a starting material UDP.
Figure 2:
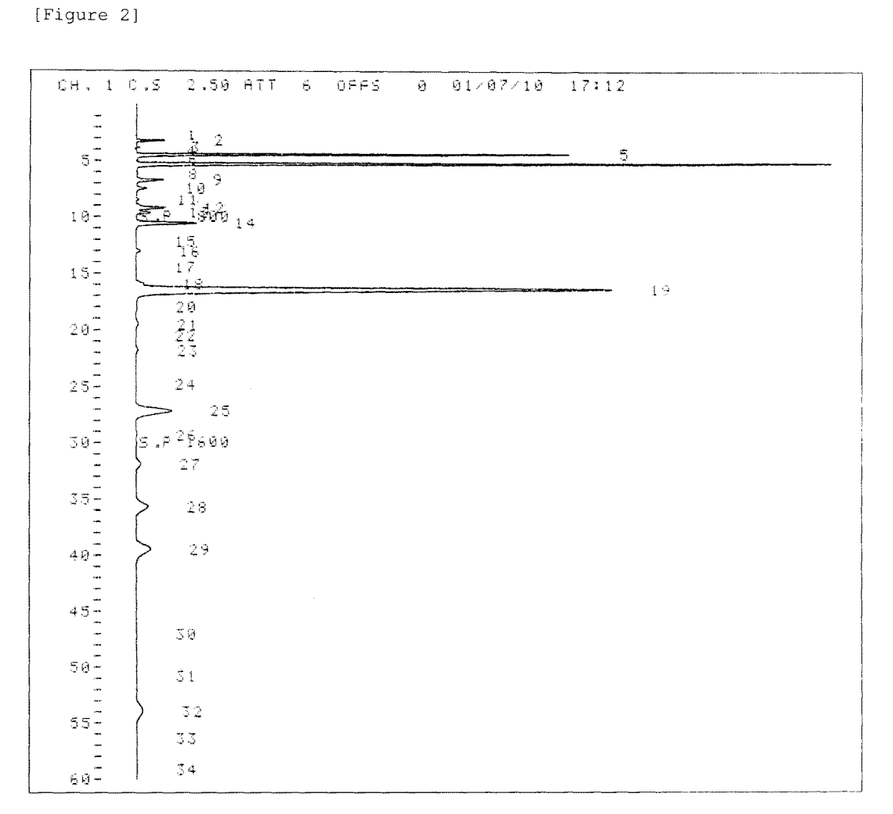
FIG. 2 illustrates an HPLC chart analyzing a product in a reaction mixture when UP$_4$U is synthesized by one pot synthesis method. In the figure, the 19$^{th}$ peak illustrates a target product UP$_4$U, and the 5$^{th}$ peak illustrates a starting material UMP.

Comparison of UP$_4$U yield and production level of impurities when using one pot synthesis method and the method of the present invention The yield of the final product was each compared when UP$_4$U was each synthesized using one pot synthesis method that is a synthesis method which improves conventional method and avoids a step using UTP free, and the method of the present example. The method of the present example was in accordance with the method of Example 1 above. The synthesis by the one pot synthesis method which changes the conventional method was performed by the following step.
(1) Preparation of Synthesis Solution 1
Tri-n-butylamine (2.2 ml, 9.2 mmol) was added to a 2.05 M aqueous UMP free solution (2.1 ml, 4.3 mmol), and the mixed solution was stirred for 20 minutes, then azeotropically dehydrated with N,N-dimethylacetamide (DMAC) four times. The residue was dissolved in DMAC (5.5 ml), and diphenyl chlorophosphate (DPC) (1.1 ml, 5.2 mmol) was added thereto at 10° C., and the mixture was stirred at room temperature for 1 hour. Tri-n-butylamine (4.1 ml, 17.2 mmol) was added thereto, and the mixture was stirred at room temperature for 10 minutes to prepare Synthesis solution 1.
(2) Preparation of Synthesis Solution 2
Tri-n-butylamine (2.2 ml, 9.2 mmol) and DMAC (3.0 ml) were added to a 0.95 M aqueous pyrophosphoric acid-triethylamine salt solution (9.0 ml, 8.5 mmol), then the mixed solution was azeotropically dehydrated with pyridine three times. Tri-n-butylamine (0.4 ml, 2.8 mmol) and pyridine (4.0 ml) were added to the residue to prepare Synthesis solution 2.
(3) Preparation of UMP-TBA Solution
Tri-n-butylamine (1.7 ml, 6.9 mmol) was added to a 2.05 M aqueous UMP free solution (3.1 ml, 6.4 mmol), and the mixed solution was stirred for 20 minutes, then azeotropically dehydrated with N,N-dimethylacetamide (DMAC) four times. The residue was dissolved in DMAC (3.5 ml) to prepare a UMP-TBA solution.
(4) Preparation of UP$_4$U Synthesis Solution
Synthesis solution 1 was added dropwise to Synthesis solution 2 at room temperature, and the mixture was stirred at room temperature for 1 hour (it was confirmed by HPLC analysis that UTP was produced about 60%). N,N-Diisopropylcarbodiimide (2.3 ml, 17.0 mmol) was added thereto, and the mixture was stirred at room temperature for 3 hours. Thereafter, the UMP-TBA solution and magnesium chloride-hexahydrate (1.7 g, 8.4 mmol) were added thereto, and the mixture was stirred at 0° C. for 1 hour, and at room temperature for 19 hours. Water (20 ml) was added thereto at 0° C., then the mixed solution was stirred at room temperature for 1 hour. The mixture was concentrated under reduced pressure, then water (50 ml) was added thereto, and the mixture was left to stand at room temperature for 2 hours. The precipitate was removed by filtration to prepare a UP$_4$U solution. UP$_4$U was quantitatively determined by HPLC, and the yield from UMP was calculated as 42%.
(Discussion of Results—Yield)
As a result, while the yield from UDP was 87% when UP$_4$U was synthesized by the method of the present examples, as shown in Example 1 described above, the yield from UMP was only 42% in the one pot synthesis method. Thus, it was revealed that the method of the present invention achieves markedly high yield, as compared to the one pot synthesis method.
(Discussion of Results—By-Product)
Furthermore, in order to compare the difference of production levels of impurities in the method of the present example and the one pot synthesis method, the product in the reaction solution after synthesizing UP$_4$U by each method was analyzed by HPLC. HPLC charts are shown in [FIG. 1] and [FIG. 2]. As is clear from FIGS. 1 and 2, in the one pot synthesis method, by-products other than UP$_4$U that is a product or UMP that is a starting material was generated about 48% at the ratio of the area of the HPLC chart, and also the number of the kind of by-products is high. On the other hand, in the method of the present invention, the ratio of by-products other than UP$_4$U or UDP that is a starting material is clearly lowered as 4.8%, and also the number of the kind of by-products is very low. Thus, in the method of the present invention, generation of by-product can be markedly reduced, thus the product can be efficiently synthesized, and isolation and purification are also easy.

Based on the comparison as described above, it was shown that the method of the present invention produces fewer impurities as compared to the one pot synthesis method, and gives a markedly improved yield, thus is very suitable as the industrial mass production method of UP$_4$U.

Comparative Test 4

Comparison of UP$_4$U Yield and Production Level of Impurities when Using Old Diimidazolyl Pyrophosphate Method and the Method of the Present Invention
The yield of the final product was each compared when UP$_4$U was each synthesized using old imidazolide method and the method of the present example. The method of present example was in accordance with the method of Example 8 above. The synthesis by the old imidazolide method was performed by the following step. Also, regarding the catalyst used in the reaction, (1) the case of adding no catalyst in the reaction, and (2) the case of using zinc chloride or (3) the case of using tetrazole as a catalyst have been studied, in reference to known methods (refer to Patent Document 2 and Non Patent Document 2).
(1) Case of No Catalyst
Tributylamine (0.95 ml, 4.0 mmol) and formamide (2.0 ml) were added to an aqueous solution of 1.09 M pyrophosphoric acid-triethylamine salt (1.86 ml, 2.0 mmol), and the mixed solution was azeotropically dehydrated four times with dimethylformamide. The resulting residue was dissolved in dimethylformamide (8.0 ml), and carbonyldiimidazole (0.97 g, 6.0 mmol) was added thereto, then the mixture was stirred at room temperature for 1 hour. Water (0.2 ml) was added to the mixture under ice cooling, and further, a 2.0 M aqueous hydrochloric acid solution (1.5 ml) was added dropwise thereto (pH 7). The mixture was concentrated under reduced pressure, and further azeotropically dehydrated twice with dimethylformamide to prepare an anhydrous diimidazolyl pyrophosphate solution.

Tributylamine (3.56 ml, 15.0 mmol) was added to an aqueous UMP-free solution (2.03 M, 2.47 ml, 5.0 mmol), and the mixed solution was azeotropically dehydrated four times with dimethylformamide, then dimethylformamide (2.0 ml) was added thereto to prepare an anhydrous UMP-tributylamine solution. This solution was added to the anhydrous diimidazolyl pyrophosphate solution, and the mixed solution was concentrated under reduced pressure and stirred at 25° C. for 48 hours. Water was added to the mixture to prepare a 50 ml aqueous solution, and the resulting aqueous solution was quantitatively determined by HPLC analysis, and the yield of $UP_4U$ was calculated as 10%.

(2) Case of Using Zinc Chloride as Catalyst

Tributylamine (0.95 ml, 4.0 mmol) and formamide (2.0 ml) were added to an aqueous solution of 1.09 M pyrophosphoric acid-triethylamine salt (1.86 ml, 2.0 mmol), and the mixed solution was azeotropically dehydrated four times with dimethylformamide. The resulting residue was dissolved in dimethylformamide (8.0 ml), and carbonyldiimidazole (0.97 g, 6.0 mmol) was added thereto, then the mixture was stirred at room temperature for 1 hour. Water (0.2 ml) was added to the mixture under ice cooling, and further, a 2.0 M aqueous hydrochloric acid solution (1.5 ml) was added dropwise thereto (pH 7). The mixture was concentrated under reduced pressure, and further azeotropically dehydrated twice to prepare an anhydrous diimidazolyl pyrophosphate solution.

Tributylamine (3.56 ml, 15.0 mmol) was added to an aqueous UMP-free solution (2.03 M, 2.47 ml, 5.0 mmol), and the mixed solution was azeotropically dehydrated four times with dimethylformamide, then dimethylformamide (2.0 ml) was added thereto to prepare an anhydrous UMP-tributylamine solution. This solution was added to the anhydrous diimidazolyl pyrophosphate solution, and zinc chloride (1.34 g, 9.8 mmol) was further added, then the mixed solution was concentrated under reduced pressure and stirred at 25° C. for 5 hours. Water was added to the mixture to prepare a 50 ml aqueous solution, and the resulting aqueous solution was quantitatively determined by HPLC analysis, and the yield of $UP_4U$ was calculated as 17%.

(3) Case of Using Tetrazole as Catalyst

Tributylamine (0.95 ml, 4.0 mmol) and formamide (2.0 ml) were added to an aqueous solution of 1.09 M pyrophosphoric acid-triethylamine salt (1.86 ml, 2.0 mmol), and the mixed solution was azeotropically dehydrated four times with dimethylformamide. The resulting residue was dissolved in dimethylformamide (8.0 ml), and carbonyldiimidazole (0.97 g, 6.0 mmol) was added thereto, then the mixture was stirred at room temperature for 1 hour. Water (0.2 ml) was added to the reaction mixture under ice cooling, and further, a 2.0 M aqueous hydrochloric acid solution (1.5 ml) was added dropwise thereto (pH 7). The mixture was concentrated under reduced pressure, and further azeotropically dehydrated twice to prepare an anhydrous pyrophosphoric acid-diimidazolide solution.

Tributylamine (3.56 ml, 15.0 mmol) was added to an aqueous UMP-free solution (2.03 M, 2.47 ml, 5.0 mmol), and the mixed solution was azeotropically dehydrated four times with dimethylformamide, then dimethylformamide (2.0 ml) was added thereto to prepare an anhydrous UMP-tributylamine solution. This solution was added to the anhydrous pyrophosphoric acid-diimidazolide solution, and 1H-tetrazole (0.5 g, 7.2 mmol) was further added, then the mixed solution was concentrated under reduced pressure and stirred at 25° C. for 19 hours. Water was added to the reaction liquid to prepare a 50 ml aqueous solution, and the resulting aqueous solution was quantitatively determined by HPLC analysis, and the synthesis yield of $UP_4U$ was calculated as 9%.

(4) Discussion of Results—Yield

To summarize the synthesis yield of $UP_4U$ in the old diimidazolide pyrophosphate method and the method of the present invention, it was as shown in the [Table 5] as described below. More specifically, it was revealed that the method of the present invention achieves markedly high yield, as compared to the old diimidazolide pyrophosphate method that is a known method.

TABLE 5

| Method | Yield of $UP_4U$ |
|---|---|
| Old diimidazolide pyrophosphate method (no catalyst) | 10% |
| Old diimidazolide pyrophosphate method (catalyst: zinc chloride) | 17% |
| Old diimidazolide pyrophosphate method (catalyst: tetrazole) | 9 |
| Method of present invention (Example 8) | 51% |

(5) Discussion of Results—By-Product

Figure 3:
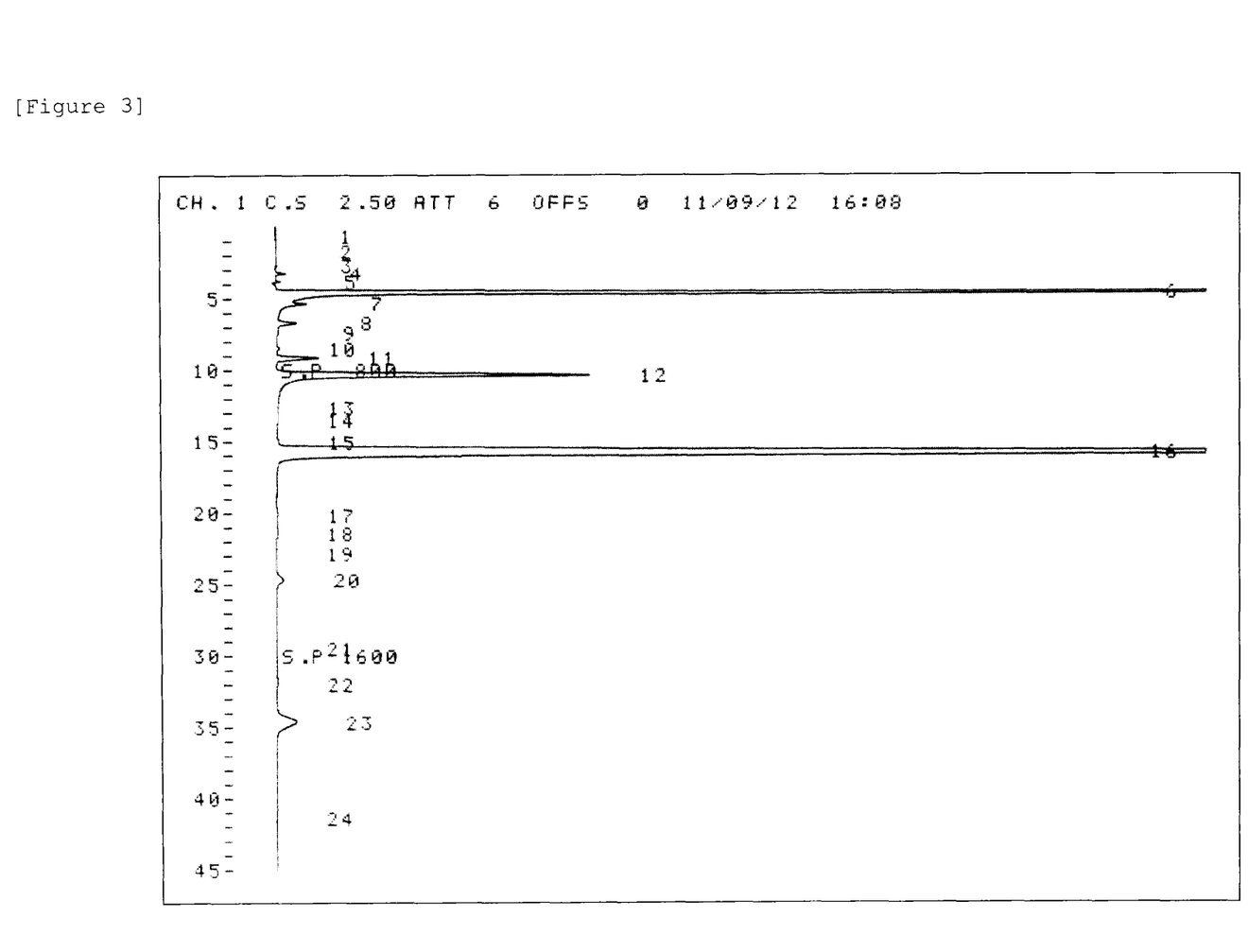
FIG. 3 illustrates an HPLC chart analyzing a product in a reaction mixture when UP$_4$U is synthesized by the method of the present invention. In the figure, the 16$^{th}$ peak illustrates a target product UP$_4$U, and the 6$^{th}$ peak illustrates a starting material UMP.
Figure 4:
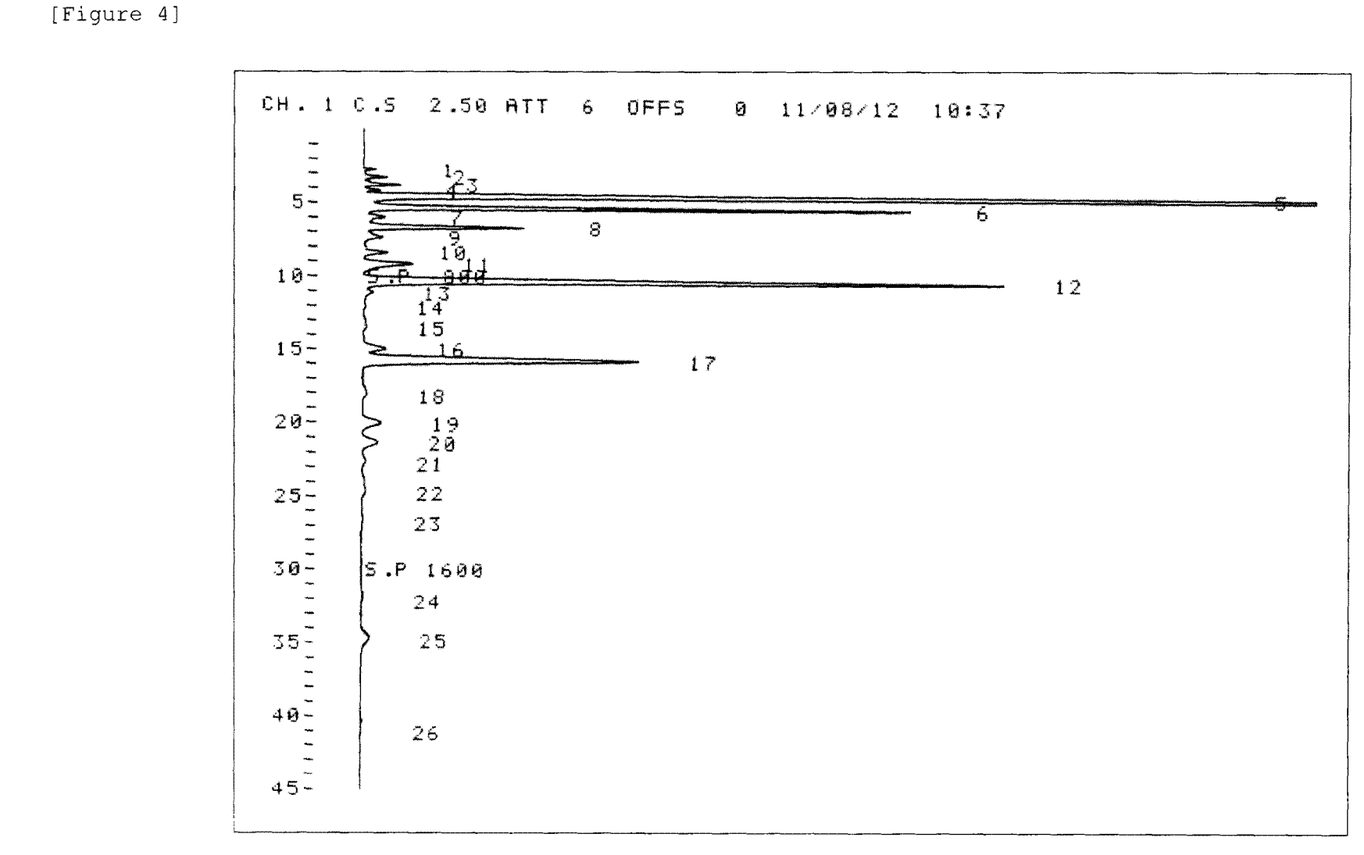
FIG. 4 illustrates an HPLC chart analyzing a product in a reaction mixture when UP$_4$U is synthesized by old diimidazolyl pyrophosphate method (no catalyst). In the figure, the 17$^{th}$ peak illustrates a target product UP$_4$U, and the 5$^{th}$ peak illustrates a starting material UMP.
Figure 5:
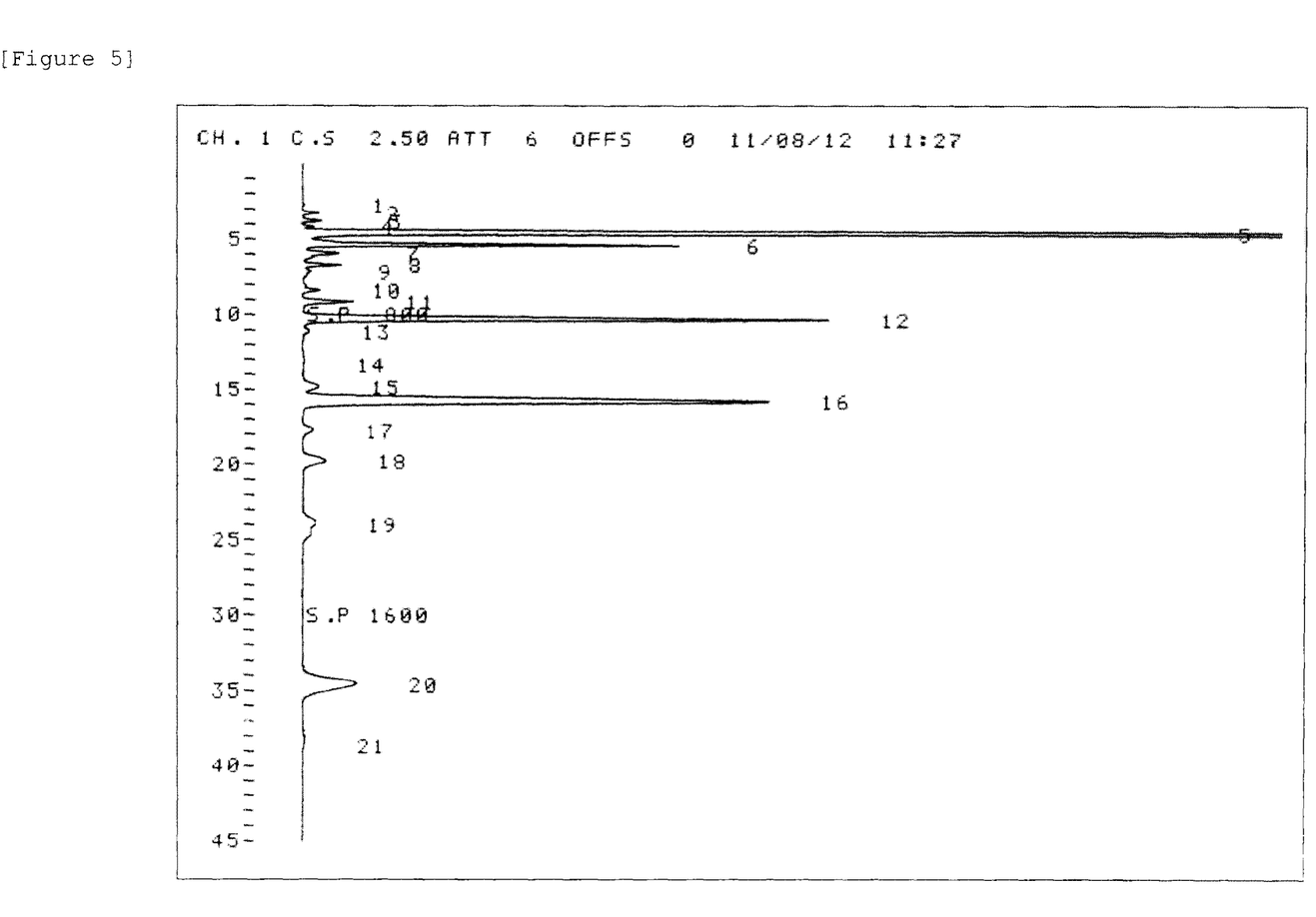
FIG. 5 illustrates an HPLC chart analyzing a product in a reaction mixture when UP$_4$U is synthesized by old diimidazolyl pyrophosphate method (catalyst ZnCl$_2$). In the figure, the 16$^{th}$ peak illustrates a target product UP$_4$U, and the 5$^{th}$ peak illustrates a starting material UMP.
Figure 6:
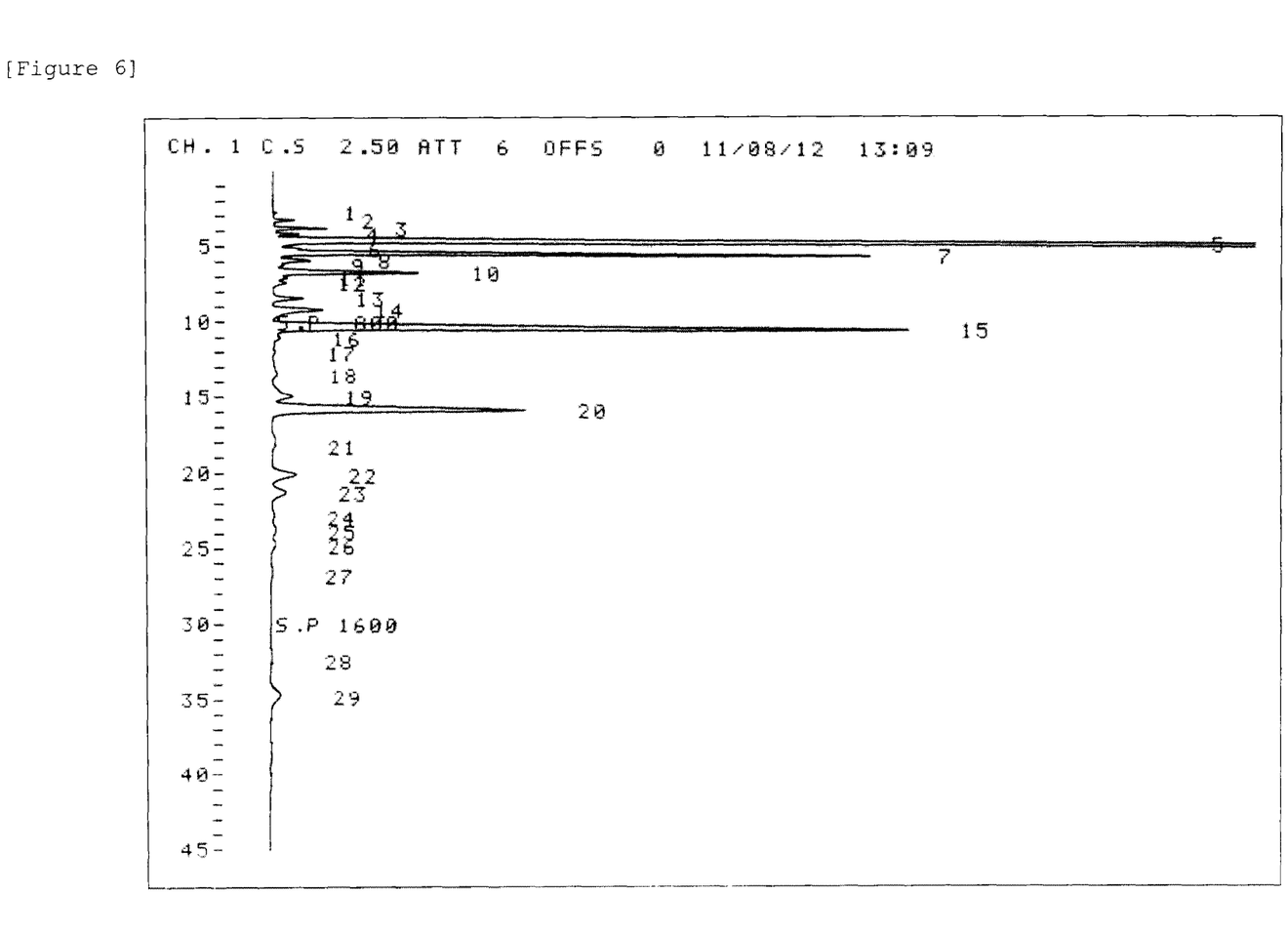
FIG. 6 illustrates an HPLC chart analyzing a product in a reaction mixture when UP$_4$U is synthesized by old diimidazolyl pyrophosphate method (catalyst tetrazole). In the figure, the 20$^{th}$ peak illustrates a target product UP$_4$U, and the 5$^{th}$ peak illustrates a starting material UMP.

Furthermore, in order to compare the difference of production levels of impurities in the method of the present invention and the old diimidazolide pyrophosphate method, the product in the reaction liquid after synthesizing $UP_4U$ by each method was analyzed by HPLC. HPLC charts are shown in [FIG. 3] to [FIG. 6]. Also, in the old diimidazolide pyrophosphate method and the method of the present example, the ratio of the by-products other than $UP_4U$ that is a product or UMP that is a starting material in the area of HPLC chart is as shown in the [FIG. 6] described below.

As is clear from FIGS. 3 to 6 and Table 6, in the old diimidazolyl pyrophosphate method, by-products other than $UP_4U$ that is a product or UMP that is a starting material was generated as much as about 40% at the ratio of the area of the HPLC chart, and also the number of the kind of by-products is high. On the other hand, in the method of the present invention, the ratio of by-products other than $UP_4U$ or the UMP that is a starting material is clearly lowered as 16%, and also the number of the kind of by-products is very low. Thus, in the method of the present invention, generation of by-product can be markedly reduced, thus the product can be efficiently synthesized, and isolation and purification are also easy.

TABLE 6

| Method | Ratio of area of by-product |
|---|---|
| Old diimidazolyl pyrophosphate method (no catalyst) | 40% |
| Old diimidazolyl pyrophosphate method (catalyst: zinc chloride) | 39% |
| Old diimidazolyl pyrophosphate method (catalyst: tetrazole) | 41% |
| Method of present invention (Example 8) | 16% |

Based on the comparison as described above, it was shown that the method of the present invention produces fewer impurities as compared to the old diimidazolyl pyrophosphate method, and gives a markedly improved yield, thus is very suitable as the industrial mass production method of $UP_4U$.

The present invention has been described above, based on the examples. The examples are merely examples, and it is understood by a person skilled in the art that various modifications are possible, and the modifications are also in the scope of the present invention.

For example, in the above examples, an aqueous ferric chloride solution was used as the aqueous solution containing metal ion was used, but it is not an intent to particularly limit, and an aqueous solution dissolving (i) ferrous chloride, ferric chloride, ferric bromide, aluminum trichloride, cerium trichloride, lanthanum trichloride, and the like as examples of the metal halide, (ii) inorganic salts of sulfate, nitrate, perchloric acid and the like of a metal selected from the group consisting of iron (divalent), iron (trivalent), aluminum, cerium and lanthanum as examples of the metal inorganic salt, or (iii) trifluoromethanesulfonate, acetate, trifluoroacetate, citrate and the like of a metal selected from the group consisting of iron (divalent), iron (trivalent), aluminum, cerium and lanthanum as examples of the metal organic salt can be suitably used. A person skilled in the art can easily understand that the yield of $UP_4U$ is improved as well as the above examples also when the aqueous solution containing these metal ions is used.

The invention claimed is:

1. A method for producing $P^1,P^4$-di(uridine 5'-)tetra phosphate, the method comprising reacting a phosphoric acid-activating compound represented by the following formula [II] or [III]:

with a phosphoric acid compound selected from the group consisting of UMP, UDP, UTP and a pyrophosphoric acid or a salt thereof (excluding UTP free) in water or a hydrophilic organic solvent, in the presence of a metal ion selected from the group consisting of an iron (II) ion, an iron (III) ion, a trivalent aluminum ion, a trivalent lanthanum ion, and a trivalent cerium ion, wherein:
$R^1$ represents a uridyl group binding to the 5'-position,
X represents a heterocyclic group selected from the group consisting of an imidazolyl group, a benzimidazolyl group and a 1,2,4-triazolyl group;
n represents an integer of 1 or 2; and
the reacting is conducted at a reaction pH of less than 7.

2. The production method according to claim 1, wherein:
the phosphoric acid-activating compound is UDP-imidazolide; and
the phosphoric acid compound is UDP or a UDP salt.

3. The production method according to claim 1, wherein:
the phosphoric acid-activating compound is UMP-imidazolide; and
the phosphoric acid compound is a UTP salt.

4. The production method according to claim 1, wherein:
the phosphoric acid-activating compound is UMP-imidazolide; and
the phosphoric acid compound is a pyrophosphoric acid or pyrophosphate.

5. The production method according to claim 1, wherein:
the phosphoric acid-activating compound is diimidazolyl pyrophosphate; and
the phosphoric acid compound is UMP or a UMP salt.

6. The production method according to claim 1, wherein the metal ion is selected from the group consisting of an iron (II) ion, an iron (III) ion and an aluminum ion.

7. The production method according to claim 6, wherein the metal ion is an iron (III) ion or an aluminum ion.

8. The production method according to claim 1, wherein the metal ion is provided in the form of chloride, bromide, nitrate, sulfate or acetate of the metal.

9. The production method according to claim 1, comprising reacting the phosphoric acid-activating compound represented by formula [II] with said phosphoric acid compound.

10. The production method according to claim 1, comprising reacting the phosphoric acid-activating compound represented by formula [III] with said phosphoric acid compound.

* * * * *